United States Patent [19]

Suzuki et al.

[11] 4,318,885

[45] Mar. 9, 1982

[54] LIQUID TREATING DEVICE FOR CHEMICAL ANALYSIS APPARATUS

[75] Inventors: Nobuyoshi Suzuki, Hachioji; Shigeru Yoshinari, Tokyo, both of Japan

[73] Assignee: Olympus Optical Co., Ltd., Tokyo, Japan

[21] Appl. No.: 184,320

[22] Filed: Sep. 5, 1980

[30] Foreign Application Priority Data

Sep. 10, 1979 [JP] Japan .................. 54-115105
Oct. 8, 1979 [JP] Japan .......... 54-138339[U]

[51] Int. Cl.³ ....................... G01N 1/14; G01N 27/26
[52] U.S. Cl. ........................... 422/68; 422/63; 422/100; 134/22 C
[58] Field of Search ............ 422/50, 68, 81, 63, 422/100; 204/1 T, 195 R; 134/22 C

[56] References Cited

U.S. PATENT DOCUMENTS 3,607,094  9/1971  Beer ............................ 422/63
3,622,279 11/1971  Moran ......................... 422/65
3,707,455 12/1972  Derr et al. .
4,049,382  9/1977  Ross, Jr. et al. ............. 422/68
4,130,394 12/1978  Negersmith ............ 422/100 X
4,228,831 10/1980  Kerns .

Primary Examiner—Ronald Serwin
Attorney, Agent, or Firm—Stevens, Davis, Miller & Mosher

[57] ABSTRACT

A liquid treating device for chemical analysis apparatus which is provided with a nozzle for successively sucking various kinds of liquids such as a test liquid, wash liquid, reagent, standard liquid having a known ion concentration or the like and having one end connected to a liquid sucking means and another end operative to be penetrated into a liquid to be treated, said nozzle being surrounded by a cylindrical cell provided at its upper and lower end portions with branch pipes selectively connected to a wash liquid supply means. When both the liquid sucking means and wash liquid supply means are operative, the inner and outer wall of the nozzle are washed with the washed liquid.

6 Claims, 5 Drawing Figures

LIQUID TREATING DEVICE FOR CHEMICAL ANALYSIS APPARATUS

BACKGROUND OF THE INVENTION

1. Field of the Invention

This invention relates to a liquid treating device for chemical analysis apparatus which is provided with a nozzle for successively sucking various kinds of liquids such as a test liquid, wash liquid, reagent, standard liquid having a known ion concentration or the like and which can effectively prevent contamination between successive liquids to be treated.

2. Description of the Prior Art

Various chemical analysis apparatus which are provided with a nozzle for sucking a number of test liquids in succession and in which these test liquids are fed to a flow cell or discharged into a reaction pipe so as to effect a desired measurement have heretofore been proposed.

In such analysis apparatus, it is necessary to effectively prevent contamination between successive test liquids in order to accurately effect the desired measurement on the successive test liquids. To this end, a liquid treating device which is operative to move the nozzle to a washing position other than a test liquid sucking position or test liquid discharging position after a given treatment has been completed for one test liquid and spray a wash liquid against the outer wall of the nozzle and discharge the wash liquid from the nozzle so as to wash the inner and outer walls of the nozzle has been proposed. Another liquid treating device which makes use of a dilute liquid as the wash liquid in the case of discharging the test liquid from the nozzle into the reaction pipe and which is operative to discharge the test liquid together with the dilute liquid into the reaction pipe so as to wash the inner wall of the nozzle and clean the outer wall of the nozzle by another means such as wiping treatment or the like.

But, the former liquid treating device has the disadvantage that since provision must be made of a separate washing position and the nozzle is required to be moved to this position, the device is complex in construction and troublesome in operation. Whereas, the latter liquid treating device has the disadvantage that since it is impossible to sufficiently wash the inner wall of the nozzle by the dilute liquid having a given dilution ratio and the outer wall of the nozzle must be cleaned by another means, the device is also complex in construction and troublesome in operation.

A so-called flow-through type ion concentration measuring apparatus comprising a flow cell provided with a comparative electrode and an ion sensor selectively sensitive to a specified ion and operative to suck a test liquid through a nozzle into the flow cell so as to measure a specified ion concentration of the test liquid has heretofore been proposed. In such ion concentration measuring apparatus, in order to accurately measure the ion concentration of the successive test liquids, it is required to effectively prevent contamination between successive test liquids in the nozzle, flow cell and liquid transfer pipe interposed between these nozzle and flow cell and to always effect measurement on the basis of a correct calibration line. In order to satisfy these two requirements, another liquid treating device has been proposed in which a nozzle is moved to a washing position after the ion concentration of one test liquid has been measured and a wash liquid is sprayed against the outer wall of the nozzle and the wash liquid is sprayed out of the nozzle through the flow cell and liquid transfer pipe in a direction opposed to the sucking direction of the test liquid, thereby washing the inner and outer walls of the nozzle, liquid transfer pipe and flow cell.

In the above mentioned ion concentration measuring apparatus, use is made of two kinds of standard liquids having different known ion concentrations and such ion concentrations are measured at two calibration points and a line drawn through these two points defines a calibration line. The calibration line may be defined at a suitable time, for example, prior to measurement of a plurality of successive test liquids. But, in order to effect an accurate measurement on each test liquid, it is preferable that two kinds of standard liquids are measured in the course of measuring the successive test liquids to correct the calibration line and that prior to the measurement of each test liquid, the measurement on either one of the standard liquids is effected to correct the calibration line.

But, the use of the measures described above for prevention of contamination, correction of calibration line or the like provides the disadvantage that the device is complex in construction and troublesome in operation.

Meanwhile, in almost all of the conventional flow-through type ion concentration measuring apparatus, when the apparatus is ready for measurement, the flow cell becomes vacant. If the flow cell is vacant, the comparative electrode and the electrode portions of the ion sensor become dried and are deteriorated in their characteristics, and as a result, the apparatus can not effect accurate measurement and provides a material decrease in durability.

SUMMARY OF THE INVENTION

An object of the invention, therefore, is to provide a liquid treating device for chemical analysis apparatus which can eliminate the above mentioned drawbacks which have been encountered with the prior art techniques, which is simple in construction and which can effectively prevent contamination between successive liquids to be treated.

A feature of the invention is the provision of a liquid treating device for chemical analysis apparatus comprising a nozzle for sucking a liquid to be treated thereinto, a cylindrical member surrounding the front end portion of the nozzle and arranged displaceably relative to the nozzle, means for relatively displacing the cylindrical member and nozzle in axial direction thereof, and a wash liquid supply means for supplying a wash liquid into the cylindrical member, whereby the wash liquid supply means is made operative when the front end portion of the nozzle is located in the cylindrical member to supply the wash liquid into the cylindrical member and the wash liquid is sucked into the nozzle, thereby washing the inner and outer walls of the nozzle.

In a preferred embodiment of a liquid treating device for chemical analysis apparatus according to the invention which is applied to apparatus for measuring the ion concentration of successive test liquids with the aid of two kinds of standard liquids having different known ion concentrations, use may be made of an ion sensor constructed as an insulation gate transistor which has recently been developed in the semiconductor industry.

This ion sensor is composed of a field effect transistor provided at its gate portion with an insulation ion sensitive film formed of $SiO_2$, $Si_3O_4$ or the like and selectively sensitive to a specified ion. In such ion sensor, one semiconductor substrate may be coated with an ion sensitive film sensitive to one kind of ion or may be coated with a plurality of ion sensitive films sensitive to different kinds of ions, that is, coated with a plurality of insulation gate portions. All of these sensors can easily be formed by a conventional method used in semiconductor industry and have an excellent durability and are small in size. As a result, the above mentioned apparatus for measuring the ion concentration of successive test liquids which makes use of such ion sensor can effect a desired measurement by using a minute amount of test liquid and the apparatus as a whole is small in size.

Further objects and features of the invention will be fully understood from the following detailed description with reference to the accompanying drawings, wherein:

DETAILED DESCRIPTION OF THE PREFERRED EMBODIMENTS

Figure 1:
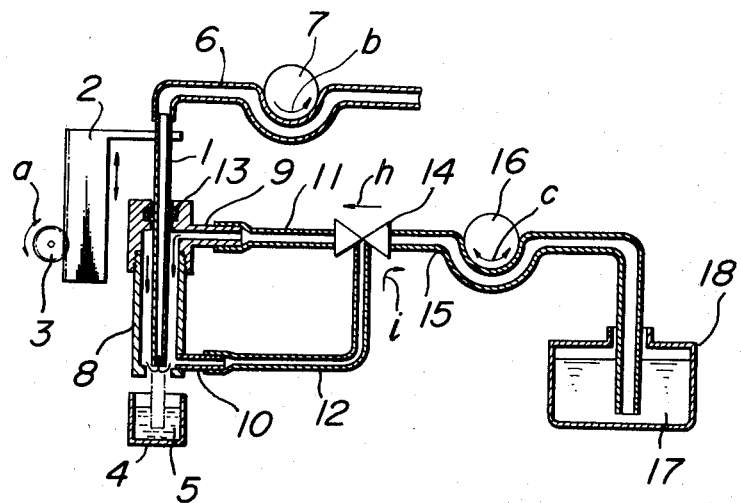
FIG. 1 is a cross-sectional view of one embodiment of a liquid treating device for chemical analysis apparatus according to the invention.

FIG. 1 shows one embodiment of a liquid treating device for chemical analysis apparatus according to the invention. In the present embodiment, a nozzle 1 for sucking a test liquid is detachably held by one end of a rack 2 displaceable in a vertical direction. With the rack 2 is threadedly engaged a pinion gear 3 secured to an output shaft of a motor not shown and selectively rotatable in directions shown by arrow a. If the motor is energized to rotate the pinion gear 3 in a given direction, the rack 2 causes the nozzle 1 to selectively move downwardly and hence to be penetrated into a liquid, for example, a test liquid 5 such as serum enclosed in a container 4. To the nozzle 1 is connected one end of a liquid transfer pipe 6 the other end of which is connected to a liquid sucking means composed of a roller pump 7 selectively rotatable in a direction shown by an arrow b. The roller pump 7 functions to suck the test liquid 5 when it is rotated. The other end of the liquid transfer pipe 6 is connected through a flow cell not shown, for example, to a waste liquid container not shown.

Provision is made of a fixed cylindrical member 8 which surrounds that front end portion of the nozzle 1 which is penetrated into the test piece when the nozzle 1 is located at its upper dead position shown in FIG. 1. The nozzle 1 is extended through the fixed cylindrical member 8 and made movable in its axial direction.

The fixed cylindrical member 8 is provided at its upper and lower end portions with branch pipes 9, 10, respectively, to which are connected one end of respective transfer pipes 11, 12. In addition, the fixed cylindrical member 8 is provided inside the upper end portion thereof located above the branch pipe 9 with a resilient body 13 such as an O-ring or the like engaged with the nozzle 1. The nozzle 1 is made closely slidable with the resilient body 13 so as to prevent the test liquid from leaking through the upper end of the cylindrical member 8.

The other ends of the branch pipes 9, 10 connected to the cylindrical member 8 are connected to a three way valve 14, respectively. To the remaining inlet of the three way valve 14 is connected a transfer pipe 15 the other end of which is connected through a roller pump 16 selectively rotatable in directions shown by arrows c to a wash liquid container 18 enclosing a wash liquid 17 therein.

The liquid treating device shown in FIG. 1 will operate as follows. In the present embodiment, that condition under which the front end portion of the nozzle 1 is formed with an air layer and the nozzle 1 and liquid transfer pipe 6 are filled with the wash liquid is a condition ready for sucking the test liquid.

In the first place, the motor not shown is energized to rotate the pinion gear 3 by a given amount in a clockwise direction to move the rack 2 downwardly so as to penetrate the nozzle 1 into the test liquid 5. Then, the roller pump 7 is rotated by a given amount in the directions shown by the arrow b, thereby sucking a given amount of test liquid 5 into the nozzle 1. Subsequently, the pinion gear 3 is rotated by a given amount in a counterclockwise direction to cause that portion of the nozzle 1 which is filled with the test liquid to move upwardly into the cylindrical member 8. Then, the roller pump 7 is rotated again in the direction shown by the arrow b to transfer the test liquid thus sucked into the nozzle 1 to a flow cell not shown, for example, which functions to effect a desired measurement.

After the desired measurement of the test liquid has been effected, the three way valve 14 is made open in a direction shown by arrow h and the roller pump 16 is rotated in a clockwise direction to feed the wash liquid 17 from the container 18 through the transfer pipes 15, 11 and branch pipe 9 into the cylindrical member 8, thereby washing the outer wall of the nozzle 1. At the same time, the roller pump 7 is rotated in the direction shown by the arrow b at a speed which is higher than the rotary speed of the roller pump 16. As a result, the wash liquid 17 fed into the cylindrical member 8 by the rotation of the roller pump 16 passes through the outer wall of the nozzle 1 in a direction shown by an arrow in FIG. 1 and is sucked into the nozzle 1 without dropping from the lower end opening of the cylindrical member 8. Then, the wash liquid passes through the nozzle 1, liquid transfer pipe 6 and flow cell not shown into the waste liquid container not shown. The use of such washing steps ensures a washing treatment of the inner and outer walls of the nozzle 1, liquid transfer pipe 6, and flow cell.

The roller pump 7 is stopped after a given amount of the wash liquid 17 has passed through the nozzle 1, liquid transfer pipe 6 and flow cell. At a time which is a little earlier than the time at which the roller pump 7 is stopped, the roller pump 16 is rotated in a counterclockwise direction and at the same time the three way valve 14 is made open in a direction shown by an arrow i, thereby causing the wash liquid 17 in the cylindrical member 8 to feed back into the container 18.

As a result, when both the roller pumps 7, 16 stop their rotations, an air layer is formed in the front end portion of the nozzle 1. This is the above mentioned condition ready for sucking the test liquid.

Then, the same steps as mentioned above are repeated to effect the desired measurement on the successive test liquids.

As stated hereinbefore, the liquid treating device according to the invention is capable of causing a given amount of wash liquid 17 to flow through the outer and inner walls of the nozzle 1 and liquid transfer pipe 6, of discharging the wash liquid adhered to the outer wall of the nozzle 1 by reversing the rotation of the roller pump 16 and of forming an air layer in the front end portion of the nozzle 1, thereby effectively preventing contamination between the successive test liquids and between the test liquid and the wash liquid 17.

Figure 2:
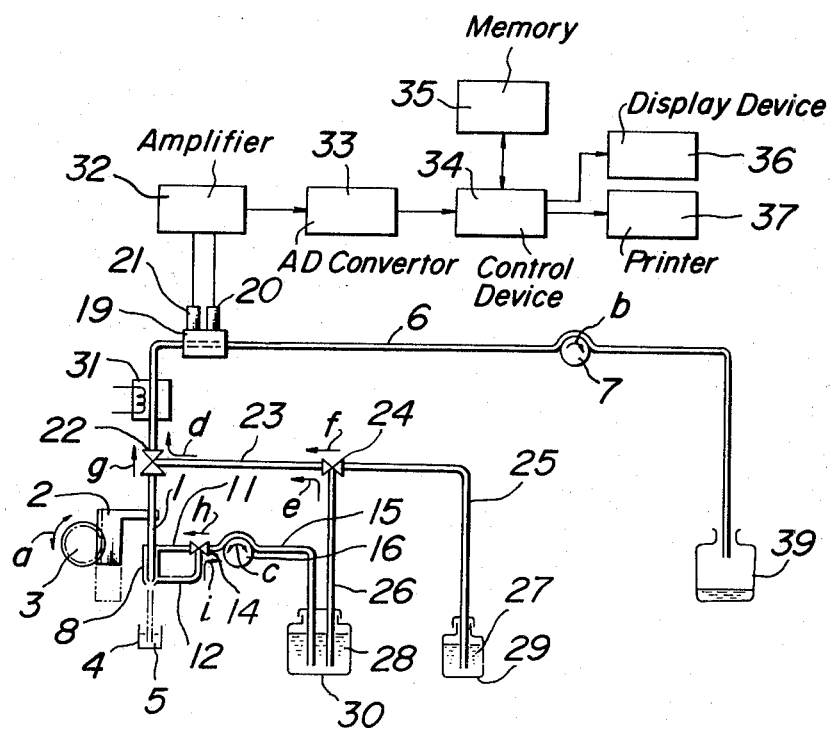
FIG. 2 is a diagrammatic view of another embodiment of a liquid treating device for chemical analysis apparatus according to the invention.

FIG. 2 shows another embodiment of a liquid treating device for chemical analysis apparatus according to the invention.

In the present embodiment, the liquid transfer pipe 6 is provided at that portion thereof which lies between the nozzle 1 and the roller pump 7 with a flow cell 19 which is provided with a comparative electrode 20 and an ion sensor 21 constructed as above mentioned insulation gate transistor such that a liquid contact portion of the comparative electrode 20 and an ion sensitive portion of the ion sensor 21 are brought into contact with the test liquid sucked into and enclosed in the flow cell 19. The nozzle 1 is connected through one inlet of a three way valve 22 to the liquid transfer pipe 6. To the other inlet of the three way valve 22 is connected one end of a standard liquid transfer pipe 23 the other end of which is connected to another three way valve 24 the remaining two inlet of which are connected through transfer pipes 25, 26 to first and second standard liquid containers 29, 30 enclosing therein first and second standard liquids 27, 28 having known different ion concentrations. In addition, the liquid transfer pipe 6 is provided at that portion which lies between the three way valve 22 and the flow cell 19 with a heat exchanger 31 constructed so as to maintain the liquid to be sucked into the flow cell 19 at a given temperature.

The outputs, for example, electric potentials, corresponding to the ion concentrations of the successive test liquids detected by the comparative electrode 20 and ion sensor 21 are supplied through an amplifier 32 and AD converter 33 to a control device 34 such as a computer or the like. The control device 34 functions to perform a given operational treatment on the basis of the calibration line which shows the concentration as a function of the electric potential and which has been stored beforehand in a memory 35. The result of such operational treatment is displayed by a display device 36 and printed out by a printer 37. In order to define the calibration line, the first and second standard liquids 27, 28 are sucked into the cell flow 19 in succession to measure respective electric potentials which are then stored in the memory 35. Then, the control device 34 is operated to effect the operational treatment on the function of the electric potential and concentration on the basis of the calibration line thus defined and to store the calibration line in the memory 35.

The ion concentration measuring apparatus shown in FIG. 2 will operate as follows. The flow cell 19 shown in FIG. 2 is provided with one ion sensor 21 only, but a flow cell 19 provided with three ion sensors 21A, 21B, 21C secured to respective insulating resin blocks 38 and arranged in axial direction as shown in FIG. 3A and arranged in radial direction as shown in FIG. 3B will be described with reference to their operations for simultaneously measuring three ions of $Na^+$, $K^+$ and $Cl^-$.

In the first place, the operations of defining the calibration line will be described. The three way valve 22 is made open in a direction shown by an arrow d and the three way valve 24 is made open in a direction shown by an arrow e. The roller pump 7 is rotated for a given time in a direction shown by the arrow b to suck the second standard liquid 28 into the flow cell 19 and respective electric potentials corresponding to the concentrations of $Na^+$, $K^+$, $Cl^-$ are stored in the memory 35. Then, the three way valve 24 is made open in a direction shown by an arrow f and the roller pump 7 is rotated for a given time in the same direction shown by the arrow b to suck the first standard liquid 27 into the flow cell 19, respective electric potentials corresponding to the concentrations of $Na^+$, $K^+$, $Cl^-$ being stored in the memory 35. Subsequently, the control device 34 is operated to define a calibration line for each ion on the basis of the electric potential for each ion of the first and second standard liquids 27, 28 stored in the memory 35, this calibration line being stored in the memory 35. After the calibration line has been defined, the three way valve 24 is made open again in the direction shown by the arrow e to suck the second standard liquid 28 into at least the flow cell 19. As a result, the comparative electrode 20 and ion sensor 21 are immersed into the second standard liquid 28, thereby completing preparations for measuring ion concentration of the test liquid.

In the case of measuring the ion concentration of the test liquid, the motor not shown is energized to rotate the pinion gear 3 by a given amount in a clockwise direction to move the rack 2 downwardly so as to penetrate the nozzle 1 into the test liquid 5.

Figure 3:
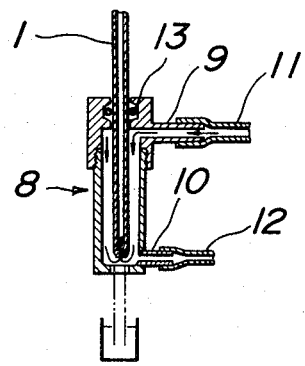
FIG. 3 is an enlarged cross-sectional view of a cylindrical member shown in FIGS. 1 and 2.
Figure 4A:
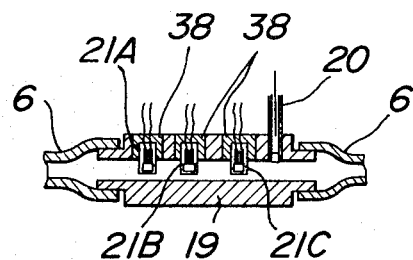
FIG. 4A is an enlarged cross-sectional view of one embodiment of a flow cell shown in FIG. 2.
Figure 4B:
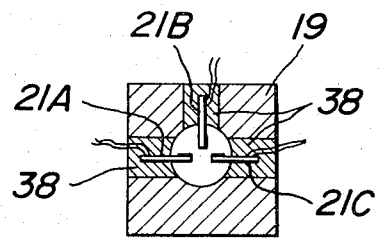
FIG. 4B is an enlarged cross-sectional view of another embodiment of a flow cell shown in FIG. 2.

Then, the three way valve 22 is made open in a direction shown by an arrow g and the roller pump 7 is rotated by a given amount in the direction shown by the arrow b, thereby sucking a given amount of test liquid 5 into the nozzle 1. Subsequently, the pinion gear 3 is rotated by a given amount in a counterclockwise direction to cause that portion of the nozzle 1 which is filled with the test liquid to move upwardly into the cylindrical member 8 as shown in FIGS. 2 and 3. Then, the roller pump 7 is rotated again in the direction shown by the arrow b to transfer the test liquid sucked into the nozzle 1 to the flow cell 19 in which the ion sensors 21A, 21B, 21C shown in FIGS. 3A and 3B function to detect respective electric potentials of $Na^+$, $K^+$, $Cl^-$ in the test liquid. Then, the control device 34 is operated to effect a given operational treatment on the basis of respective electric potentials thus detected and respective calibration lines which have been stored beforehand in the memory 35. The result of the operational treatment is displayed by the display device 36 and printed out by the printer 37.

After the measurement of the ion concentration of the test liquid has been effected, the three way valve 14 is made open in a direction shown by an arrow h and the roller pump 16 is rotated in a counterclockwise direction to feed the second standard liquid 28 through the transfer pipes 15, 11 and branch pipe 9 into the cylindrical member 8, thereby washing the outer wall of the nozzle 1. At the same time, the roller pump 7 is rotated in the direction shown by the arrow b at a speed which is higher than the rotary speed of the roller pump 16. As a result, the second standard liquid 28 fed into the cylindrical member 8 by the rotation of the roller pump 16 passes through the outer wall of the nozzle 1 in a direction shown by an arrow in FIG. 3 and is sucked into the nozzle 1 without dropping from the lower end opening of the cylindrical member 8. As a result, the second standard liquid 28 is fed through the nozzle 1, liquid transfer pipe 6 and flow cell 9 into a waste liquid container 39. The use of such washing steps ensures a washing treatment of the inner and outer walls of the nozzle 1, liquid transfer pipe 6, and flow cell 19 and comparative electrode 20 and ion sensors 21A, 21B, 21C held by te flow cell 19. The roller pump 7 is stopped after a given amount of the second standard liquid 28 has passed through the nozzle 1, liquid transfer pipe 6 and flow cell 19. At a time which is a little earlier than the time at which the roller pump 7 is stopped, the roller pump 16 is rotated in a clockwise direction and at the same time the three way valve 14 is made open in a direction shown by an arrow i, thereby causing the second standard liquid 17 in the cylindrical member 8 to feed back into the container 30.

As a result, when both the roller pumps 7, 16 stop their rotations at least the flow cell 19 is filled with the second standard liquid and an air layer is formed in the front end portion of the nozzle 1. This is the condition ready for measuring the ion concentration of the test liquid.

Then, the same steps as mentioned above are repeated to measure the ion concentration of the successive test liquids.

The operations of the motor for rotating the pinion gear 3, roller pumps 7, 16 and three way valves 14, 22, 24 may be controlled by the control device 34, for example.

As stated hereinbefore, the liquid treating device according to the present invention has a number of advantages. In the first place, since the flow cell 19 is always filled with the second standard liquid 18 under the condition ready for measuring the test liquid, it is possible to effectively prevent deterioration of the characteristics and durability of the comparative electrode 20 and ion sensors 21A, 21B, 21C and rapidly start the measurement. Secondly, after the ion concentration of the test liquid has been measured, a given amount of the second standard liquid 28 passes through the outer and inner walls of the nozzle 1, liquid transfer pipe 6 and flow cell 19, the reverse rotation of the rotary pump 16 causes the second standard liquid adhered to the outer wall of the nozzle 1 to be discharged and the air layer is formed in the front end portion of the nozzle 1, so that it is possible to effectively prevent contamination between the successive test liquids and between the test liquid and the second standard liquid 18. Third, the first and second standard liquids 27, 28 having known different ion concentrations are selectively sucked into the flow cell 19, so that the calibration line can automatically be corrected at any desired time or at a given time dependent on a program prepared beforehand. Fourth, the flow cell 19 is filled with the second standard liquid 28 under the condition ready for measuring the test liquid, so that if the second standard liquid 28 is measured prior to the measurement of the test liquid every time or every given cycle when the test liquid is measured, the calibration line defined beforehand can be corrected, and a result, it is possible to effect an accurate measurement. Fifth, at the raised up position of the nozzle 1, the second standard liquid 18 passes along the outer wall of the nozzle 1 and then is sucked thereinto and subsequently flows through the liquid transfer pipe 6 and cell 19 in the same direction as the sucking direction of the test liquid so as to clean these members and the three way valves 22, 24 are changed over to correct the calibration line, so that the device is relatively simple in construction. Finally, the temperature of the test liquid and first and second standard liquids to be sucked into the cell 19 is maintained at a given temperature by means of the heat exchanger 21, so that it is always possible to effect accurate measurement.

The invention is not limited to the above mentioned embodiment only, but various changes and modification may be made. For example, the above mentioned ion sensor constructed as a plurality of independent insulation gate transistors may be composed of a plurality of ion sensitive portions formed on one semiconductor substrate or may be composed of a conventional glass electrode or the like which has widely been used in practice. In the above mentioned embodiment, in the case of defining the calibration line the second standard liquid 28 is sucked through the three way valves 24, 22 into the flow cell 19. Alternatively, the second standard liquid 28 may be sucked from the cylindrical member 8 through the nozzle 1 into the flow cell 19 in the same manner as in the case of cleaning the nozzle 1, liquid transfer pipe 6 and flow cell 19 by the second standard liquid 28. In this case, it is not necessary to provide the three way valve 24, so that the device becomes simple in construction. Similarly, the first standard liquid 27 may be sucked from the nozzle 1, if desired. In this case, it is not necessary to provide the three way valve 22, so that the device as a whole becomes simple in construction. In addition, in the above mentioned embodiment, the nozzle 1 is made upwardly and downwardly movable relative to the cylindrical member 8. Conversely, the cylindrical member 8 may be made upwardly and downwardly movable relative to the nozzle 1. In this case, when the cylindrical member 8 is located at its raised position, the container 4 may be moved upwardly to penetrate the nozzle 1 into the test liquid 5 and cause the nozzle 1 to suck the test liquid thereinto. In addition, in the above mentioned embodiment, the test liquid sucked into the nozzle 1 is fed into the flow cell 19 so as to effect the desired measurement. But, the liquid treating device according to the invention may also be effectively applied to the chemical analysis apparatus in which the nozzle 1 is horizontally moved and the test liquid sucked into the nozzle 1 is discharged into the reaction pipe so as to effect the desired measurement or to the chemical analysis apparatus in which desired reagent is selectively sucked from a number of reagents into the nozzle 1 and then discharged therefrom. Moreover, as the test liquid sucking means, use may be made of a syringe instead of the roller pump 7.

What is claimed is:

1. A liquid treating device for chemical analysis apparatus comprising a nozzle for sucking a liquid to be treated thereinto, a liquid transfer pipe having one end connected to said nozzle, a liquid sucking means connected to the end of said liquid transfer pipe, a cylindrical member for surrounding the front end portion of said nozzle and arranged displaceably relative to said nozzle, means for displacing said nozzle relative to said cylindrical member in the axial direction thereof, and a wash liquid supply means selectively connected to said cylindrical member and for supplying a wash liquid into said cylindrical member, whereby said wash liquid supply means is operative when the front end portion of said nozzle is located in said cylindrical member to supply said wash liquid into said cylindrical member and said liquid sucking means is operative to suck said wash liquid into said nozzle, thereby washing the inner and outer walls of said nozzle.

2. The device according to claim 1 and further comprising a flow cell arranged in that portion of said liquid transfer pipe which lies between said nozzle and said liquid sucking means and provided with a comparative electrode and an ion sensor selectively sensitive to a specified ion, a standard liquid supply means selectively connected to that portion of said liquid transfer pipe which lies between said ion concentration measuring means and said nozzle and supplying a first standard liquid having a known ion concentration to said ion concentration measuring means when said liquid sucking means is operative, a standard liquid supply means selectively connected to said cylindrical member and for supplying a second standard liquid having a known ion concentration which is different from that of said first standard liquid to said cylindrical member, whereby when said nozzle is located in said cylindrical member, said standard liquid supply means and liquid sucking means are operative to cause said second standard liquid to flow through said cylindrical member, nozzle and liquid transfer pipe so as to clean the inner and outer walls of said nozzle, liquid transfer pipe and ion concentration measuring means.

3. The device according to claim 1, wherein said cylindrical member is provided at is upper and lower end portion with branch pipes to which are selectively connected through a three way valve said wash liquid supply means.

4. The device according to claim 2, wherein said comparative electrode and ion sensor are connected through an amplifier, AD converter to a control device composed of a computer and connected to a memory, display device and printer, said control device being operative to perform a given operational treatment on the basis of calibration lines stored beforehand in said memory and representing ion concentration as a function of electric potentials detected by said ion sensor and the result of said operational treatment being displayed by said display device and printed out by said printer.

5. The device according to claim 2, wherein said flow cell is provided with a plurality of ion sensors secured to respective insulating resin blocks and arranged in axial direction.

6. The device according to claim 2, wherein said flow cell is provided with a plurality of ion sensors secured to respective insulating resin blocks and arranged in radial direction.

* * * * *